United States Patent
Sweeney

(10) Patent No.: US 9,949,777 B2
(45) Date of Patent: Apr. 24, 2018

(54) METHOD AND DEVICE FOR DELIVERING MEDICINE TO BONE

(71) Applicant: Spinal Generations, LLC, Mokena, IL (US)

(72) Inventor: Patrick J. Sweeney, Flossmoor, IL (US)

(73) Assignee: Spinal Generations, LLC, Mokena, IL (US)

(*) Notice: Subject to any disclaimer, the term of this patent is extended or adjusted under 35 U.S.C. 154(b) by 911 days.

(21) Appl. No.: 13/886,945

(22) Filed: May 3, 2013

(65) Prior Publication Data
US 2013/0245602 A1 Sep. 19, 2013

Related U.S. Application Data

(63) Continuation-in-part of application No. 13/270,072, filed on Oct. 10, 2011, now Pat. No. 9,445,852, which
(Continued)

(51) Int. Cl.
*A61B 17/86* (2006.01)
*A61B 17/88* (2006.01)
(Continued)

(52) U.S. Cl.
CPC ........ *A61B 17/864* (2013.01); *A61B 17/7061* (2013.01); *A61B 17/8685* (2013.01);
(Continued)

(58) Field of Classification Search
CPC . A61B 17/68; A61B 17/7061; A61B 17/8685; A61B 17/8805; A61B 17/8819;
(Continued)

(56) References Cited

U.S. PATENT DOCUMENTS 3,310,051 A   3/1967   Schulte
4,399,814 A   8/1983   Pratt et al.
(Continued)

FOREIGN PATENT DOCUMENTS

EP   0 858 775   8/1998
EP   1 653 869   6/2011
(Continued)

OTHER PUBLICATIONS

International Search Report and Written Opinion for International Application No. PCT/US2014/035542, dated Sep. 22, 2014, 14 pages.
(Continued)

*Primary Examiner* — Bradley Osinski
*Assistant Examiner* — Nilay Shah
(74) *Attorney, Agent, or Firm* — Foley & Lardner LLP

(57) ABSTRACT

A method for the long-term delivery of fluids to a bone of a patient includes providing a cannulated bone screw and an insert configured to be coupled to the bone screw. The method further includes creating an aperture in the skin of a patient, inserting the bone screw into a bone of the patient through the aperture, and coupling the insert to the bone screw. The method further includes the steps of providing a fluid source, coupling the fluid source to the insert, and delivering a fluid from the fluid source to the insert.

11 Claims, 11 Drawing Sheets

Related U.S. Application Data is a continuation of application No. 12/822,022, filed on Jun. 23, 2010, now Pat. No. 8,062,270, which is a continuation-in-part of application No. 12/427,520, filed on Apr. 21, 2009, now Pat. No. 8,808,337, which is a continuation of application No. 10/704,526, filed on Nov. 7, 2003, now Pat. No. 7,527,611, which is a continuation-in-part of application No. 10/620,287, filed on Jul. 15, 2003, now Pat. No. 7,575,572, and a continuation-in-part of application No. 10/682,307, filed on Oct. 9, 2003, now Pat. No. 7,608,062.

(51) Int. Cl.
*A61M 37/00* (2006.01)
*A61B 17/70* (2006.01)
*A61M 39/02* (2006.01)
*A61B 17/34* (2006.01)
*A61B 17/00* (2006.01)
*A61F 2/30* (2006.01)

(52) U.S. Cl.
CPC ...... *A61B 17/8819* (2013.01); *A61B 17/8841* (2013.01); *A61M 37/00* (2013.01); *A61B 17/3472* (2013.01); *A61B 17/7098* (2013.01); *A61B 17/8833* (2013.01); *A61B 2017/00004* (2013.01); *A61F 2002/30677* (2013.01); *A61M 2039/025* (2013.01)

(58) Field of Classification Search
CPC ............ A61B 17/8833; A61B 17/8836; A61B 17/8841; A61B 17/3472; A61B 17/7098; A61M 2039/025; A61M 2039/1072; A61F 2/4601
See application file for complete search history.

(56) References Cited

U.S. PATENT DOCUMENTS

| | | | |
|---|---|---|---|
| 4,464,178 A | 8/1984 | Dalton | |
| 4,653,487 A | 3/1987 | Maale | |
| 4,653,489 A * | 3/1987 | Tronzo | A61B 17/746 606/304 |
| 4,760,844 A * | 8/1988 | Kyle | A61B 17/742 606/102 |
| 4,772,261 A * | 9/1988 | Von Hoff | A61B 17/68 604/175 |
| 4,976,692 A | 12/1990 | Atad | |
| 5,047,030 A | 9/1991 | Draenert | |
| 5,122,114 A * | 6/1992 | Miller | A61M 39/0208 604/175 |
| 5,133,755 A * | 7/1992 | Brekke | A61F 2/28 623/23.51 |
| 5,203,770 A | 4/1993 | Wigness et al. | |
| 5,372,583 A * | 12/1994 | Roberts | A61B 17/3472 600/567 |
| 5,380,319 A | 1/1995 | Saito et al. | |
| 5,425,723 A | 6/1995 | Wang | |
| 5,562,625 A * | 10/1996 | Stefancin, Jr. | A61M 5/3271 604/110 |
| 5,618,286 A | 4/1997 | Brinker | |
| 5,681,289 A | 10/1997 | Wilcox et al. | |
| 5,702,372 A | 12/1997 | Nelson | |
| 5,749,883 A | 5/1998 | Halpern | |
| 5,752,941 A * | 5/1998 | Romano' | A61L 29/06 604/265 |
| 5,769,899 A * | 6/1998 | Schwartz | A61L 27/227 606/77 |
| 5,800,407 A | 9/1998 | Eldor | |
| 5,871,484 A | 2/1999 | Spievack et al. | |
| 5,951,160 A | 9/1999 | Ronk | |
| 6,019,761 A | 2/2000 | Gustilo | |
| 6,048,343 A | 4/2000 | Mathis et al. | |
| 6,077,265 A | 6/2000 | Werding et al. | |
| 6,210,376 B1 | 4/2001 | Grayson | |
| 6,214,012 B1 | 4/2001 | Karpman et al. | |
| 6,220,888 B1 | 4/2001 | Correa | |
| 6,228,088 B1 | 5/2001 | Miller et al. | |
| 6,364,856 B1 | 4/2002 | Ding et al. | |
| 6,387,098 B1 | 5/2002 | Cole et al. | |
| 6,461,327 B1 | 10/2002 | Addis et al. | |
| 6,669,059 B2 * | 12/2003 | Mehta | A61H 35/04 222/211 |
| 6,679,890 B2 | 1/2004 | Margulies et al. | |
| 7,527,611 B2 | 5/2009 | Sweeney | |
| 7,575,572 B2 | 8/2009 | Sweeney | |
| 7,608,062 B2 | 10/2009 | Sweeney | |
| 8,057,090 B1 | 11/2011 | Saha et al. | |
| 8,062,270 B2 | 11/2011 | Sweeney | |
| 2001/0021852 A1 * | 9/2001 | Chappius | A61B 17/3472 600/300 |
| 2002/0138146 A1 | 9/2002 | Jackson | |
| 2002/0169507 A1 * | 11/2002 | Malone | A61B 17/7064 623/17.11 |
| 2003/0045885 A1 | 3/2003 | Margulies et al. | |
| 2003/0083662 A1 | 5/2003 | Middleton | |
| 2003/0139751 A1 | 7/2003 | Evans et al. | |
| 2003/0212426 A1 | 11/2003 | Olson et al. | |
| 2004/0225292 A1 | 11/2004 | Sasso et al. | |
| 2005/0015059 A1 | 1/2005 | Sweeney | |
| 2005/0015060 A1 | 1/2005 | Sweeney | |
| 2005/0059972 A1 | 3/2005 | Biscup | |
| 2006/0079905 A1 * | 4/2006 | Beyar | A61B 17/7095 606/76 |
| 2006/0111767 A1 | 5/2006 | Olson et al. | |
| 2007/0073295 A1 | 3/2007 | Biedermann et al. | |
| 2007/0083265 A1 | 4/2007 | Malone | |
| 2007/0233123 A1 | 10/2007 | Ahmad et al. | |
| 2008/0039846 A1 | 2/2008 | Lee et al. | |
| 2008/0039855 A1 | 2/2008 | Lambert | |
| 2008/0086143 A1 | 4/2008 | Seaton et al. | |
| 2009/0164016 A1 | 6/2009 | Georgy et al. | |
| 2009/0204158 A1 | 8/2009 | Sweeney | |
| 2010/0042213 A1 * | 2/2010 | Nebosky | A61B 17/56 623/16.11 |
| 2010/0106199 A1 | 4/2010 | Sawa et al. | |
| 2010/0131014 A1 | 5/2010 | Peyrot et al. | |
| 2010/0262089 A1 | 10/2010 | Sweeney | |
| 2011/0046682 A1 | 2/2011 | Stephan et al. | |

FOREIGN PATENT DOCUMENTS

| | | |
|---|---|---|
| WO | WO-02/098307 A1 | 12/2002 |
| WO | WO-2005/009258 | 2/2005 |
| WO | WO-2010/019788 | 2/2010 |
| WO | WO-2011/063240 | 5/2011 |

OTHER PUBLICATIONS

Communication received in European Patent Application No. 11250603.5, dated Feb. 20, 2015, 5 pages.
International Search Report and Written Opinion for PCT Application No. PCT/US2015/014216, dated Apr. 22, 2015, 14 pages.
International Search Report and Written Opinion for PCT Application PCT/US2013/052853, dated Jan. 14, 2014, 15 pages.
U.S. Appl. No. 12/427,520, filed Apr. 21, 2009, Patrick J. Sweeney.
U.S. Appl. No. 13/227,230, filed Sep. 7, 2011, Patrick J. Sweeney.
U.S. Appl. No. 13/270,072, filed Oct. 10, 2011, Patrick J. Sweeney.
Cecil, M.L. et al., "Projection of the S2 Pedicle Onto the Posterolateral Surface of the Ilium—A Technique for Lag Screw Fixation of Sacral Fractures or Sacroiliac Joint Dislocations," Spine 1996, vol. 21, pp. 875-878, www.kalindra.com/project.htm, 6 pages.
European Office Action for Application No. 04757057.7, dated Jan. 26, 2010, 5 pages.
European Search Report for European Patent Application No. 04757057.7, dated Jul. 2, 2010, 4 pages.
European Search Report for European Patent Application No. 04757057.7, dated Nov. 30, 2009, 3 pages.

(56) References Cited

OTHER PUBLICATIONS

European Search Report for European Patent Application No. 11250603.5-2310, dated Sep. 29, 2011, 6 pages.
Press release from Spine Center Atlanta, "New Screw Debut First-time Use for New Spinal Surgery Device," 2002, Orthopaedic & Spine Surgery of Atlanta, LLC. www.SpineCneterAtlanta.com, 2 pages.
Sato, T. et al., "Calcium Phosphate Augmentation of Screw Fixation in Femoral Neck Fracture," 47th Annual Meeting, Orthopaedic Research Society, Feb. 25-28, 2001, San Francisco, CA, 1 page.
Instratek Inc., "Titanium Cannulated Bone Screws Minimize Surgery Time by Eliminating Complicated Procedure Steps," www.instratek.com/bone_screw/, 5 pages, downloaded on May 27, 2003.
SunMedica—Orthopaedic Surgery Products, "orthoPLUG® Hard Bone Design," Redding, CA 96002; www.xunmedica.com, 1 page, known of at least by Mar. 5, 2004.
European Search Report for European Application No. 16180626.0, dated Sep. 27, 2016, 8 pages.

* cited by examiner

METHOD AND DEVICE FOR DELIVERING MEDICINE TO BONE

CROSS-REFERENCE TO RELATED PATENT APPLICATIONS

This application is a continuation-in-part of U.S. application Ser. No. 13/270,072, filed Oct. 10, 2011, which is a continuation of U.S. application Ser. No. 12/822,022, filed Jun. 23, 2010, which is a continuation-in-part of U.S. application Ser. No. 12/427,520, filed Apr. 21, 2009, which is a continuation of U.S. application No. Ser. 10/704,526, filed Nov. 7, 2003, which is a continuation-in-part of U.S. application Ser. No. 10/620,287, filed Jul. 15, 2003, and a continuation-in-part of U.S. application No. Ser. 10/682,307, filed Oct. 9, 2003, all of which are incorporated herein by reference in their entireties.

BACKGROUND

The present invention relates to devices and methods for delivering substances such as medicants to bones and to devices for removing materials from the body. More particularly, the present invention concerns devices and methods for delivering substances to the interior or exterior of fractured or otherwise injured bones, especially to the fracture interface thereof. The present invention also relates to devices and methods for removing materials from the interior or exterior of injured bone. The devices may also be used to promote fusion of a bone or a joint, including a peripheral joint such as a finger or a knee.

SUMMARY

One embodiment of the invention relates to a method for the long-term delivery of fluids to a bone of a patient. The method includes providing a threaded and cannulated bone screw having a resealable cap configured to be penetrated by a needle. The method further includes creating an aperture in the skin of a patient, inserting the bone screw into a bone of the patient through the aperture, and closing the aperture. The method further includes providing a needle coupled to a fluid source, inserting the needle through the cap and into the bone screw, and delivering a fluid from the fluid source to the bone screw via the needle.

Another embodiment of the invention relates to a method for the long-term delivery of fluids to a bone of a patient. The method includes providing a cannulated bone screw, providing an insert configured to be coupled to the bone screw, creating an aperture in the skin of a patient, inserting the bone screw into a bone of the patient through the aperture, and coupling the insert to the bone screw. The method further includes providing a fluid source, coupling the fluid source to the insert, and delivering a fluid from the fluid source to the insert.

Still another embodiment of the invention relates to a bone screw and insert system, including a bone screw having a proximal end and a distal end. The bone screw is cannulated between the proximal end and the distal end and includes an opening at the distal end. The bone screw and insert system further includes an insert configured to be slidably received within the cannulation of the bone screw and to extend out of the opening.

Still another embodiment of the invention relates to a method for curing bone cement. The method includes providing a threaded and cannulated bone screw and an insert configured to be received within the bone screw cannulation. The method further includes creating an aperture in the skin of a patient, inserting the bone screw into a bone of the patient through the aperture, and coupling the insert to the bone screw. The method further includes delivering a bone cement to an area of the bone proximate the bone screw via the insert and heating the insert to heat the bone screw and the area of the bone proximate the bone screw.

Alternative exemplary embodiments relate to other features and combinations of features as may be generally recited in the claims.

BRIEF DESCRIPTION OF THE DRAWINGS

The disclosure will become more fully understood from the following detailed description, taken in conjunction with the accompanying figures, in which:

FIG. 3($b$) is a perspective view of the bone-screw insert of FIG. 3($a$).

FIG. 8($b$) is a schematic perspective view of an IV being used to provide a liquid to a bone screw disposed in a hip bone.

FIG. 8($c$) shows a schematic perspective view of a pump assembly being used to provide a liquid to a bone screw disposed in a hip bone.

FIG. 9($b$) is a schematic cross-sectional view of the bone-screw insert of FIG. 9($a$) following delivery of a substance to the insert.

DETAILED DESCRIPTION OF THE PREFERRED EMBODIMENTS

Figure 1:
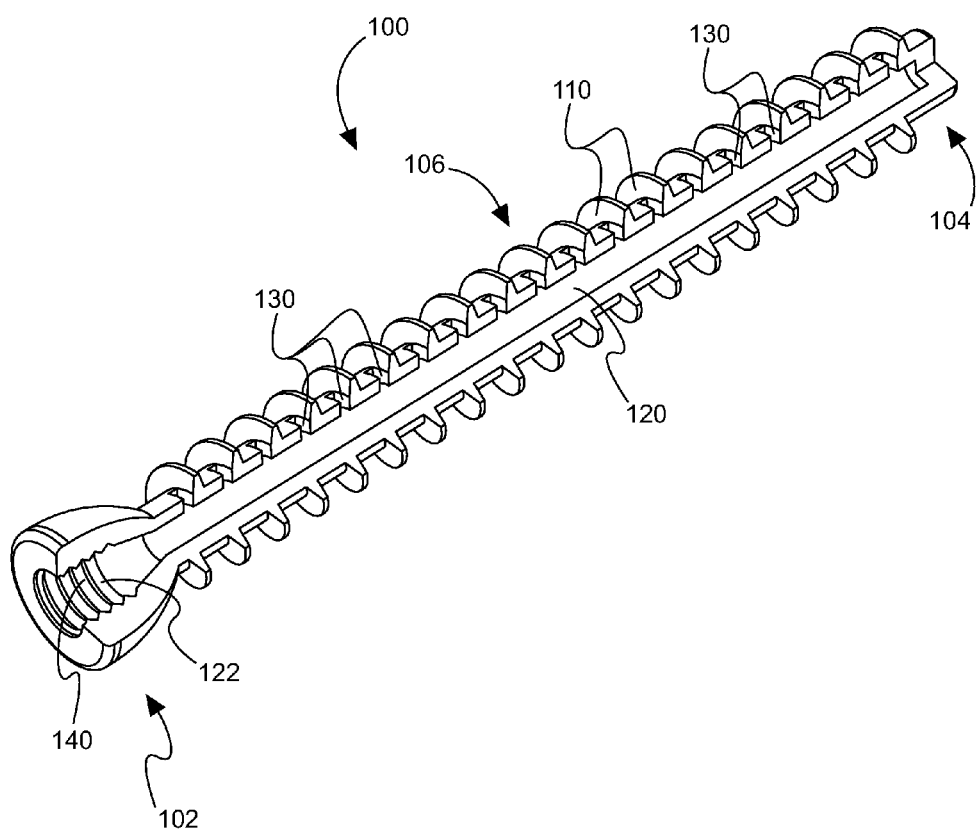
FIG. 1 is a perspective view of a bone screw according to an exemplary embodiment.

Before turning to the figures, which illustrate the exemplary embodiments in detail, it should be understood that the present application is not limited to the details or methodology set forth in the description or illustrated in the figures.

It should also be understood that the terminology is for the purpose of description only and should not be regarded as limiting.

In accordance with the present invention, a bone-screw-insert is disposed within a fenestrated bone screw or along an external surface of a bone screw, and the combination is used to deliver desired substances to the vicinity of a bone. The inserts are cannulated along at least a portion of their lengths and the bone screws may have an internal cannulation and/or one or more exterior insert attachment mechanisms running along at least a portion of their lengths. In certain embodiments, the insert may also be fenestrated or permeable to the substance to be delivered. The inserts of the present invention may be a single piece, or alternatively the insert may include several pieces or sections. In certain embodiments, the bone screw may be a fixation screw used to hold two or more bones or bone pieces in a fixed spatial relationship with respect to each other. The substances to be delivered may include medicants or therapeutics, or other substances which are desirable to deliver to the vicinity of a bone. The substance or a combination of substances may be delivered to the interior of a bone, to the exterior of a bone, to the fracture interface between two or more broken bones, or to any other location which may be facilitated by utilization of the present invention.

For the purposes of this application, the term "cannulated" means that the screw or insert includes a hollow cavity disposed inside at least part of its shaft. For example, the cavity may consist of a bore beginning at or near one end of the screw or insert and extending longitudinally into the screw or insert. Other configurations are possible, however, and the hollow cavity need not be restricted to a cylindrical shape or a circular cross-section. The cavity may extend throughout the entire length of the screw or insert, thus creating openings at each end of the screw or insert, or alternatively, the cavity may extend only partially into the interior of the screw or insert. The shape and size of the cavity may be suitably chosen to allow delivery of the desired substance through the screw or insert to the bone area of interest. When it is desired to use the cannulated portion of the screw or insert as reservoir for the substance to be delivered, for example, the cavity may be made as large as possible so long as the screw and insert maintain the structural integrity needed for introduction into the bone.

For the purposes of this application, the term "fenestration" is used broadly to include any slot, gap, or perforation that defines an opening between the inside of the cannulated portion of the screw or insert to the outside of the screw or insert whereby a desired substance may be delivered. Thus, a fenestrated screw includes an opening which defines a substance delivery pathway between the internal cannulated portion and the exterior of the screw. Likewise, a fenestrated insert is one that includes an opening which defines a substance delivery pathway between the internal cannulated portion and the exterior of the insert. In certain embodiments of the present invention where a fenestrated insert is utilized in combination with a fenestrated screw, at least one screw fenestration and at least one insert fenestration may be designed to align with each other once the screw and insert are in their appropriate configuration and position. Alignment or coordination of an insert fenestration and a screw fenestration will define a substance delivery pathway between the internal cannulated portion of the insert and the exterior of the screw.

Fenestrations will typically extend in the radial direction from the internal cannulation to the exterior of the screw or insert, but other configurations are possible. The fenestrations may be any desired shape or size desired to effect the delivery of the desired substance. For example, the fenestration cross-sections may be round, oval, or square. The fenestration cross-sections may, if desired, change shape between the inside and the outside of the screw or insert. Any number or combination of fenestrations may be located along the shaft or at the ends of the screws and inserts of the present invention. The insert fenestrations may be larger or smaller than the screw fenestrations.

An insert may have an outside diameter large enough such that the outside of the insert is pressed snuggly against the inside of the cannulation when the insert is in a bone screw in order to prevent the substance to be delivered from leaking between the insert and the bone screw and escaping through a bone screw fenestration from which it was not intended to escape. Alternatively, the insert may include one or more expandable portions along its length. In an exemplary embodiment, the expandable portions are balloons, each disposed around a portion of the insert, that may be deflated when the insert is placed into the bone screw and subsequently inflated. Upon inflation, each balloon forms a seal between the outside of the insert and the inside of the bone screw. Using this construction, one or more insert fenestrations and one or more bone screw fenestrations may be isolated between two inflated balloons, such that a substance delivered through the isolated insert fenestrations may exit only through bone screw fenestrations positioned between the inflated balloons. Inserts having different lengths and/or different balloon placements may be provided such that the appropriate insert and bone screw fenestrations may be isolated to provide an appropriate delivery pathway depending on the final position of the bone screw in a patient relative to the desired delivery location.

As an alternative to or in combination with an insert disposed within an internal cannulation in a bone screw, the devices provided herein may include an insert disposed along an exterior surface of a bone screw. Again, the insert may be cannulated and fenestrated or permeable to define a delivery pathway between one end of the cannulation and a portion of a bone. In this embodiment, a bone screw is provided with a means for securing an insert along at least a portion of an exterior surface of the bone screw. For example, the bone screw may include at least one groove, adapted to accept an insert, running along at least a portion of its exterior surface. Alternatively, the bone screw may include one or more attachment mechanisms, such as loops, hooks or the like, along at least a portion of its exterior surface. An insert may be inserted through these loops or hooks, securing the insert to the bone screw. In order to ensure that the attachment elements do not interfere with the insertion of the bone screw into the bone, they are desirably set back from the external circumferential surface of the bone screw. If the bone screw includes threads, the attachment elements desirably do not extend radially beyond the threads. The bone screws may be adapted to secure two or more inserts along their exterior surfaces. This design allows the physician to select the appropriate number and placement for the inserts, depending on the final positioning of the bone screw in a bone.

In some embodiments, a cannulated, fenestrated bone screw may be combined with an exterior insert to provide a delivery pathway between the bone-screw cannulation and the exterior of the bone screw. In this embodiment, an insert is disposed along an external surface of the bone screw and may be used to selectively cover one or more bone-screw fenestrations in order to provide a substance delivery pathway that is appropriate based on the positioning of the bone screw in a bone. For example, a delivery device may include a cannulated bone screw having an exterior groove running along at least a portion of its length and an insert adapted to slide into the groove. Fenestrations are disposed along the groove of the bone screw to allow a substance to pass from the cannulation to the exterior of the bone screw. When a chosen insert is inserted into the groove, it selectively covers those fenestrations that provide a delivery pathway to areas of the bone where delivery of the substance is not needed, while leaving unblocked those fenestrations that provide a delivery pathway to areas of the bone where delivery of the substance is desirable.

For the purposes of this application, the term "bone screw" is intended to refer to screws of all types which are presently known or hereafter devised for implantation into bone. In this regard, cancellous screws, cortical screws, and machine screws are all contemplated as being within the scope of the types of screws useful in the practice of the present invention. The bone screws will typically include threads along at least a portion of the exterior of the screw shaft, but it should be appreciated that tacks, pins, nails and the like may also be included within the definition of a bone screw for the purposes of the present invention, whether threaded or unthreaded. When threads are present, it may be found advantageous to use self-tapping threads, or alternatively, the threads can be pre-cut in the bone prior to bone-screw insertion.

For the purpose of this application, the term "long term" is intended to refer to an extended period of time, generally beyond 24 hours. Long term care, long term delivery of fluids, and long term treatment are therefore intended to refer to activities that may continue through a rehabilitation period for an injury and may continue beyond an initial stabilization and treatment phase for an injury, which may be known as acute care. While the bone screws and inserts described herein are configured to be suitable for long term use, the bone screws and inserts are also suitable for short term care. The bone screws and inserts described herein may be utilized to stabilize and provide treatment to a bone for an extended period of time and then be removed or may be permanently implanted into a bone.

Referring now to FIG. 1, a bone screw 100 has two ends 102 and 104 connected by a shaft 106, and bone screw threads 110. The cut-out of FIG. 1 reveals that the bone screw 100 includes a cannulated portion 120, and bone screw fenestrations 130 along the length of the cannulated portion 120. It will be appreciated by one skilled in the art that the fenestrations 130 need not be even spaced along the cannulated portion 120, but may be arranged in a desired pattern or frequency along the length of the cannulated portion 120. It will be further appreciated by one skilled in the art that one end 122 of the cannulated portion 120 of the bone screw 100 is configured to accept a bone screw insert. For example, the bone screw 100 may include additional threads 140 on the one end 122 of the cannulated portion 120 to promote fixation of a bone screw insert.

In one embodiment, the bone screw 100 may be a fixation screw used to hold two or more bones or bone pieces in a fixed spatial relationship with respect to each other. The bone screw 100 may be used to mend peripheral skeletal fractures or osteotomies, repair a spondyloysis or an odontoid fracture, or fuse lumbar facet joints, for example. Other beneficial uses of fixation screws, such as the bone screw 100, will be known to one skilled in the art and are to be included within the scope of the present invention.

Figure 2:
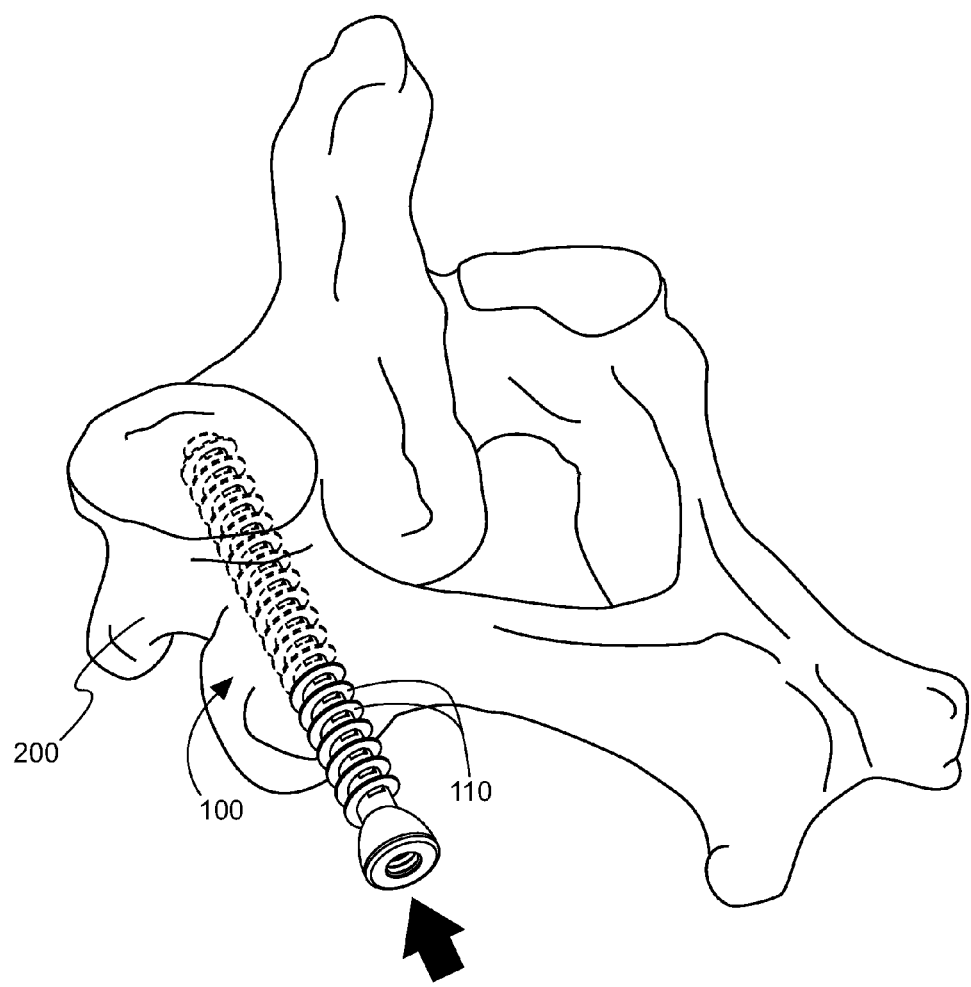
FIG. 2 is a schematic view of the a bone screw of FIG. 1 inserted into the hip bone of a patient.

Referring now to FIG. 2, the bone screw 100 is shown disposed partially within a bone 200. The bone 200 may, for example, represent a human hip bone. In one embodiment, the bone screw 100 is disposed within the bone 200 by rotating the bone screw 100 such that the bone screw threads 110 act to pull the bone screw 100 into the bone 200, thereby anchoring the bone screw 100 into place.

The bone screw 100 may include any material suitable for placement into a bone without harmful effects on the patient. Examples of suitable materials include, but are not limited to, titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalciumphosphate. Other materials useful for bone screw construction will be known to those skilled in the art, and are to be included within the scope of the present application.

In various embodiments, a bone-screw insert may be utilized. For the purposes of this application, the term "insert" is used to refer to one or more cannulated members which are disposed within or coupled to a bone screw. An insert may be disposed within the bone screw to provide for a directed or controlled delivery of a desired substance to a bone. For the purposes of this application, the term "substance" is used to refer to one or more chemical compounds that are useful when delivered to the vicinity of a bone. Substances may be chosen to help treat diseased bone as well as fractured or otherwise injured bones. Alternatively, the substance may be delivered to otherwise healthy bone to help maintain overall bone health, for example. Representative example substances include medicants or therapeutics such as antibiotics, chemotherapeutics, angiogenic factors, bone morphogenic proteins, and bone growth factors. Alternatively, the substance may be an intravenous fluid such as a saline solution or nutrition (e.g., parenteral nutrition) containing glucose, dextrose, amino acids, lipids, dietary minerals, and vitamins for delivery directly into the bloodstream. Other desirable substances may be known or hereinafter determined by one skilled in the art, and are to be included within the scope of this invention.

Figure 3A:
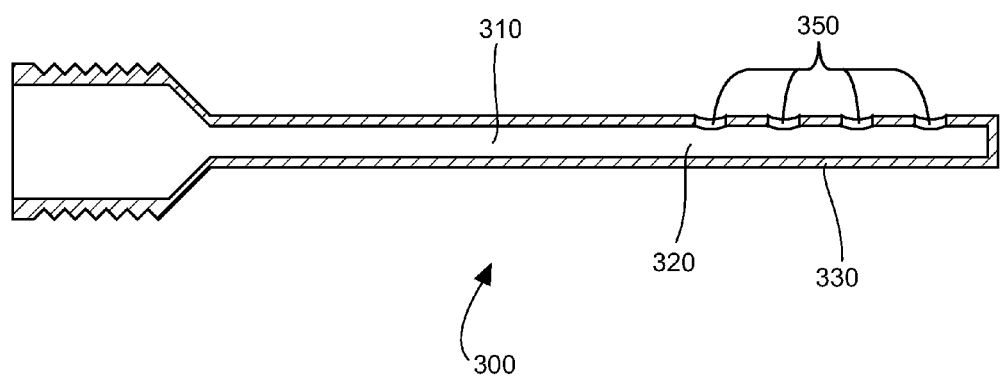
FIG. 3($a$) is a schematic cross-sectional view of a bone-screw insert with a single fenestration, according to an exemplary embodiment.
Figure 3B:
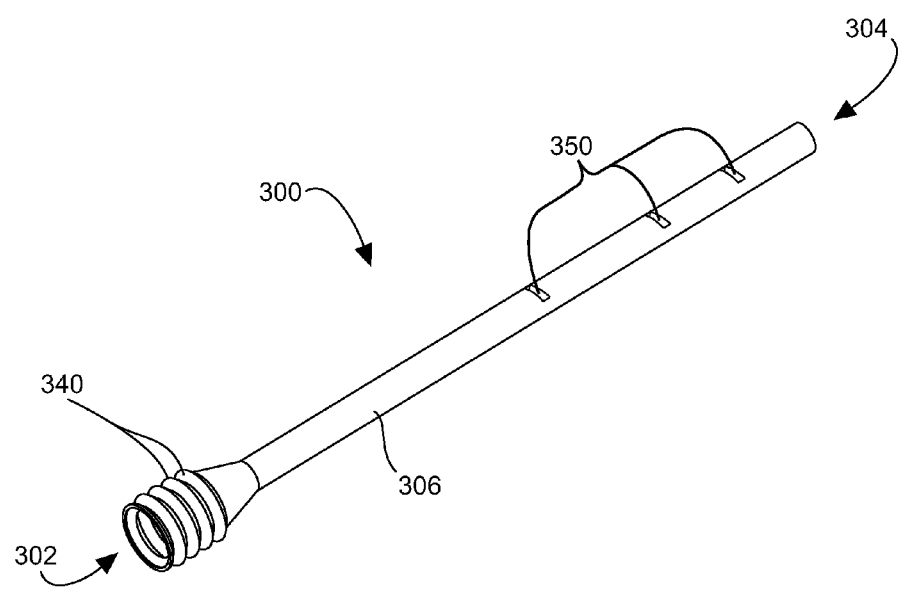

Referring now to FIG. 3(a), the insert 300 includes a cannulated portion 310 which consists of a hollow cavity 320 surrounded by the insert wall 330, where the cavity and wall dimensions may be suitably chosen in order to carry out various procedures and methods. In certain embodiments, the insert 300 may include a single piece, as disclosed in FIG. 3(a). Alternatively, the insert may include two or more pieces or sections that, when taken together, form the insert. Referring now to FIG. 3(b), when the insert 300 is a single piece, the insert includes two ends, 302 and 304, connected by a shaft 306. The shaft may be cannulated along its entire length, creating openings at each end of the insert. Alternatively, the cannulation may extend only partially into the shaft so long as the cannulation is sufficient to allow for delivery of a substance from one end of the insert to one or more bone-screw fenestrations. One end 302 of the insert 300 may include threads 340 which interlock with bone screw threads 140 of FIG. 1 to help fix an insert 300 into the bone screw 100.

In other embodiments, the insert may be otherwise coupled to the bone screw. According to an exemplary embodiment, the insert may be coupled to the bone screw via an interference fit (e.g., press fit) between the insert and the walls of the cannulation. Such an interference fit may be achieved via the expansion of the insert due to the application of heat or via the expansion of a portion of the insert. For example, the insert may include an expandable portion (e.g., a balloon). According to another exemplary embodiment, the insert may be coupled to the bone screw via a non-removable (i.e., permanent) coupling, such as an integrally formed snap feature or an adhesive. According to still another exemplary embodiment, the insert may be coupled to the bone screw with a separate coupling member, such as an external clip that engages both the insert and the bone screw to fix the position of the insert relative to the bone screw.

When the insert includes two or more pieces or sections, only one of the sections need be cannulated such that the insert sections, when taken together, allow for delivery of a substance from one end of the insert to one or more bone-screw fenestrations.

A substance may be delivered to one or more bone-screw fenestrations through an insert fenestration 350 formed in the insert wall 330. When substantially unimpeded delivery of a substance to one or more bone-screw fenestrations is desired, the inserts of the present invention may include multiple insert fenestrations 350. An insert having an appropriate number, size, shape, and location of insert fenestrations can be chosen by the practitioner to provide a delivery pathway between at least one end of the insert and the one or more bone-screw fenestrations. For example, FIG. 3(b) discloses an insert 300 having multiple insert fenestrations 350 having a substantially rectangular cross-section. Alternatively, the delivery pathway may initiate at one end of the bone screw and pass through the insert to one or more bone-screw fenestrations. The insert fenestrations need not match the bone-screw fenestrations in number, size, shape, or location, although it may be advantageous to locate at least one of the insert fenestrations such that it may be substantially aligned with at least one bone-screw fenestrations once both the bone screw and the insert are in place.

In another embodiment, the inserts may be permeable to the substance to be delivered such that the substance is delivered to the exterior of the insert by diffusion through the insert wall or through small openings in the insert wall. Such openings may be intentionally created such as by increasing the porosity of the insert material (e.g., by introducing a series of pinpricks into the material), or they may exist naturally as pores in the material. Such a permeable insert may be preferred when it is desired to effect a controlled, slow release of the desired substance to a bone, or when it is desired to prevent bone fragments, blood, fat or other materials or fluids from traveling from the exterior of the insert to the interior cavity.

Figure 4:
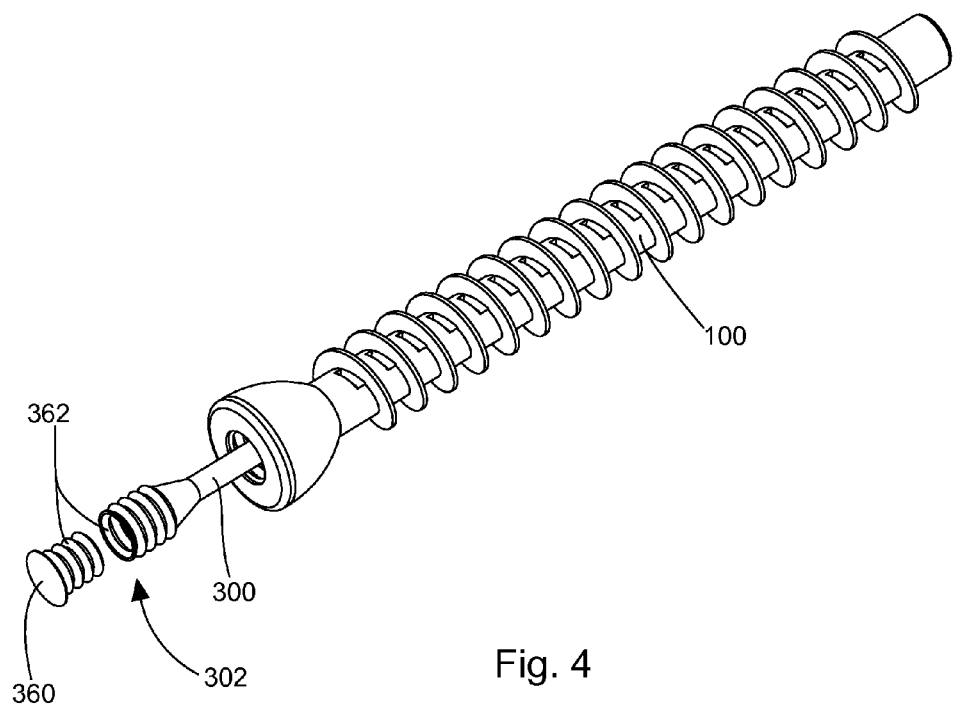
FIG. 4 is a perspective view of a bone screw, a bone-screw insert, and an insert cap, according to an exemplary embodiment.

In one embodiment, the exterior dimensions of the insert are only slightly smaller than the interior dimensions of a cannulated bone screw to provide for a tight but sliding fit when the insert is placed into the bone screw, as depicted in FIG. 4 in which the insert 300 is shown partially disposed within the bone screw 100. Also disclosed in FIG. 4 is an insert cap 360 which can be used to substantially seal the one end 302 of the insert 300 via insert cap threads 362 either before, during, or after the bone screw 100 and the insert 300 are put into place. The insert 300 may have substantially the same cross-sectional shape as the cannulated portion of the bone screw 100, or their cross-sectional shapes may be different. For example, the internal bone screw cavity and the exterior surface of the insert may have a substantially circular cross-section. One advantage of this embodiment is that after the insert 300 has been disposed within the bone screw 100, the insert 300 may be rotated with respect to the screw 100 to align one or more of the insert fenestrations 350 with one or more of the bone-screw fenestrations 130, for example. In another embodiment, the insert and bone screw may have substantially non-circular cross-sections such that the insert is not free to rotate once it has been disposed within the bone screw. In yet another embodiment, at least part of the insert cross-section may not match that of the bone screw cavity such that when the insert is disposed within the bone screw, one or more channels are formed longitudinally along at least part of the insert and bone screw shafts. Such channels may be useful, for example, to allow air or fluids to escape the bone screw cavity as the insert is introduced.

Figure 5:
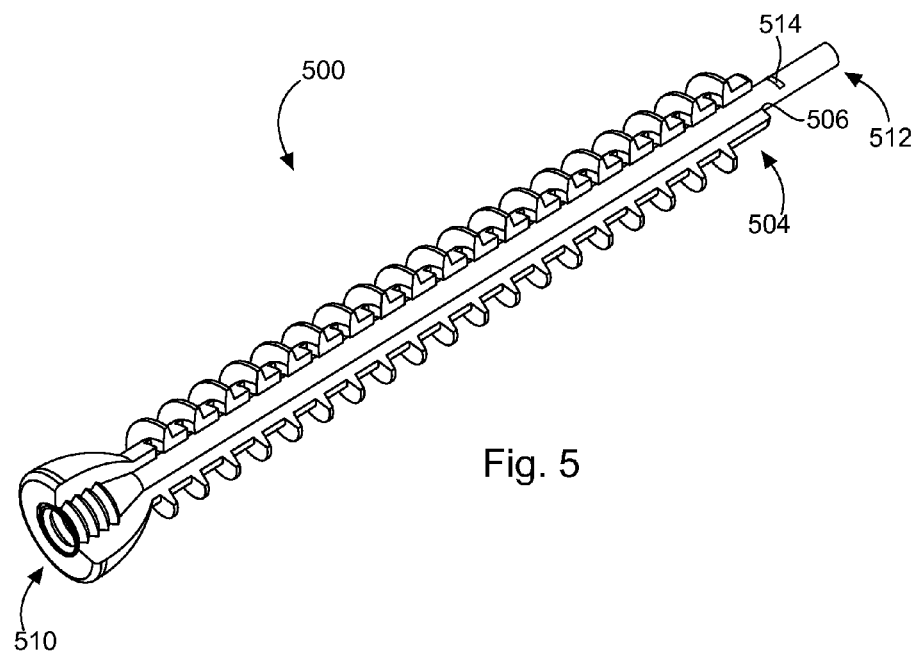
FIG. 5 is a cut-away perspective view of an insert coupled to a bone screw and extending beyond the distal end of the bone screw according to an exemplary embodiment.
Figure 6:
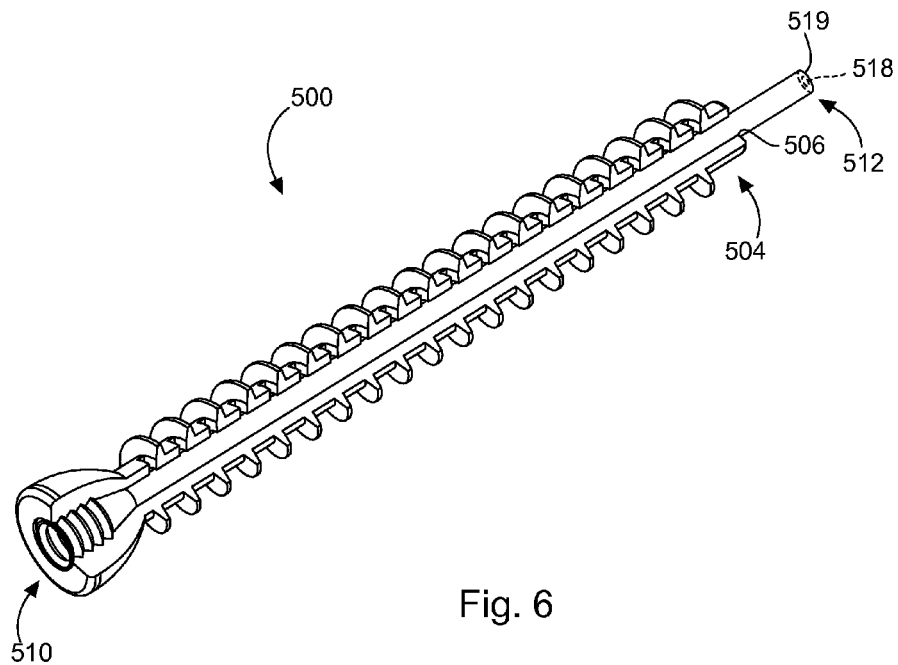
FIG. 6 is a cut-away perspective view of an insert coupled to a bone screw and extending beyond the distal end of the bone screw according to an exemplary embodiment.

Referring now to FIGS. 5-6, a bone screw 500 and an insert 510 disposed within the bone screw 500 are configured to deliver a substance to a portion of the bone beyond a distal end 504 of the bone screw 500. The distal end 504 includes an opening 506 sized similar to the hollow cavity receiving the insert 510. The insert 510 has a length greater than the length of the bone screw 500. When the insert 510 is fixed to the bone screw 500 (e.g., via threaded connection as described above) a protruding end 512 of the insert 510 extends beyond the distal end 504 of the bone screw 500 through the opening 506. The protruding end 512 may extend further into the bone (or even past the bone) in which the bone screw 500 is inserted. In one related method, the bone screw and insert embodiment shown in FIGS. 5-6 may be used to treat a diabetic foot infection, where the insert 510 extends beyond a short screw anchored in the bone to the site of the infection for treatment purposes. A substance (e.g., an antibiotic) may be delivered to the portion of the bone beyond the distal end 504 of the bone screw 500 through an opening in the protruding end 512. According to one exemplary embodiment and illustrated in FIG. 5, the opening may be an insert fenestration 514 formed in the side wall 516 of the insert 510. According to another exemplary embodiment the opening may include multiple insert fenestrations 514. According to another exemplary embodiment and illustrated in FIG. 6, the opening may be an axial fenestration 518 formed in the end wall 519 of the protruding end 512 of the insert 510. An insert having an appropriate number, size, shape, and location of insert fenestrations in the protruding end can be chosen by the practitioner to provide a delivery pathway between at least one end of the insert and the portion of the bone beyond the distal end 504. The insert 510 may have additional fenestrations configured to deliver a substance to one or more of the bone screw fenestrations. In other embodiments, the insert protruding beyond the distal end of the bone screw may be configured as a material removal device and may be connected to a material removal system allowing for removal of material from the portion of the bone beyond the distal end of the bone screw 500.

In another embodiment, the insert may be utilized to deliver liquids such as bone cements to the interior of a bone. The inserts and/or the bone screw may be further configured to facilitate the curing of a bone cement. By strategically applying heat to the portion of the bone in which the bone cement is deposited, the cure time of the bone cement can be reduced in comparison to the cure time using only body heat.

An insert, such as the insert 510 illustrated in FIGS. 5-6 may be configured to provide heat to a bone cement deposited in the bone proximate to the bone screw in which the insert is fixed. According to one exemplary embodiment, an electrical current may be applied to an insert received within or in contact with the bone screw (e.g. via a power source coupled to the insert), with the electrical resistance of the insert converting at least a portion of the electrical current to thermal energy. The insert used for such heating may or may not be the same insert used to deliver fluids to the bone screw. According to another exemplary embodiment, the insert may be heated in another manner (e.g., through submersion in a heated liquid or gas, through direct contact with a heated element, etc.) prior to being inserted into the bone screw. The bone screw may be configured to be thermally conductive or thermally insulating. A thermally conductive bone screw may be configured to transfer heat from the heated insert to the bone and the bone cement deposited in the bone. A thermally insulating bone screw may be configured to impede heat transfer from the heated insert, except through openings, such as bone screw fenestrations or in portions of the bone directly contacted by the insert, such as a portion of the bone beyond the distal end of the bone screw 500 illustrated in FIGS. 5 and 6. According to still another exemplary embodiment, the bone screw may be heated instead of or in addition to the insert to facilitate the curing of the bone cement.

Figure 7:
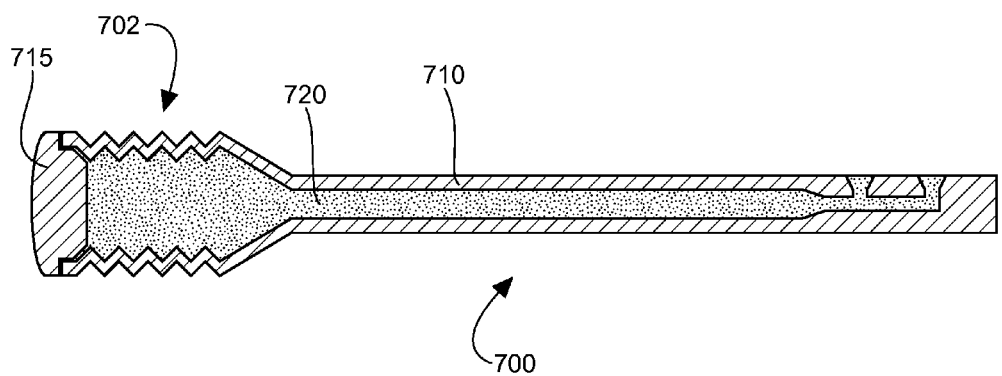
FIG. 7 is shows a schematic cross-sectional view of a bone-screw insert with an internal reservoir and a cap.

When it is desired to use the cannulated portion of the insert as a reservoir for the substance to be delivered, or when the substance is to be delivered to a bone by permeation through the insert walls, it may be desirable to make the insert walls as thin as possible. Referring now to FIG. 7, there is disclosed an insert 700 with walls 710 surrounding a reservoir 720. One end 702 of the insert 700 may be substantially sealed by an insert cap 715. For example, in one embodiment, the insert may be a thin-walled tube which increases the available volume for storage of the substance, and which also increases the diffusion of the substance through the insert wall. In another embodiment, the insert may include a film or coating on the interior surfaces of the bone-screw cavity. Inserts in accordance with this embodiment may be as thin as a few hundred nanometers or less, which again may be beneficial for increasing the reservoir size with the bone screw and insert cavity, and for increasing the diffusion of the substance through the insert wall.

In further embodiments, the inserts may control or direct the delivery of a substance to a bone through a fenestrated bone screw by substantially blocking one or more of the bone-screw fenestrations. This approach may be advantageous when it is desired to deliver the substance to a specific location with respect to the bone screw's position within the bone. Since the exact bone-screw fenestrations which align with or match this location may not be known until after the bone screw has been disposed within the bone, the bone screw inserts may allow one to selectively block the bone-screw fenestrations to which substance delivery is not desired, while maintaining a substance delivery pathway to one or more bone-screw fenestrations to which substance delivery is desired. Moreover, by utilizing an insert whereby the insert fenestrations align with the bone-screw fenestrations to which substance delivery is desired, one may achieve substantially unimpeded delivery of the substance to the area of interest.

In addition, the bone-screw inserts, even when fenestrated, may be advantageously used to significantly hinder bone fragments, blood, fat, or other materials from entering the cannulated portion of the bone screw, especially during insertion of the bone screw into the bone, for example. In this case it may be desirable to initially position the insert and bone screw such that the insert fenestrations do not align with the bone-screw fenestrations. The insert may then be subsequently re-positioned at a later time to align one or more of the insert fenestrations with the bone-screw fenestrations to facilitate substance delivery.

The inserts described herein may be formed of any material or combination of materials compatible with bone screws and may be able to be placed within bone screws without producing adverse effects to the patient. Examples of suitable insert materials include, but are not limited to, titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalciumphosphate. Other materials useful for insert construction will be known to those skilled in the art, and are to be included within the scope of the present invention. When the insert includes two or more sections, the sections need not be formed of the same material. In addition, when it is desired that the insert be permeable to the substance to be delivered, one or more of the insert sections may be formed of a material specifically chosen to impart the desired level of permeability to the insert.

The insert may be sold or otherwise provided in a kit containing two or more inserts having different fenestrations or permeability characteristics. The availability of such a kit has the advantage of allowing a practitioner to select an appropriate insert based on the particular needs of the patient.

Figure 8A:
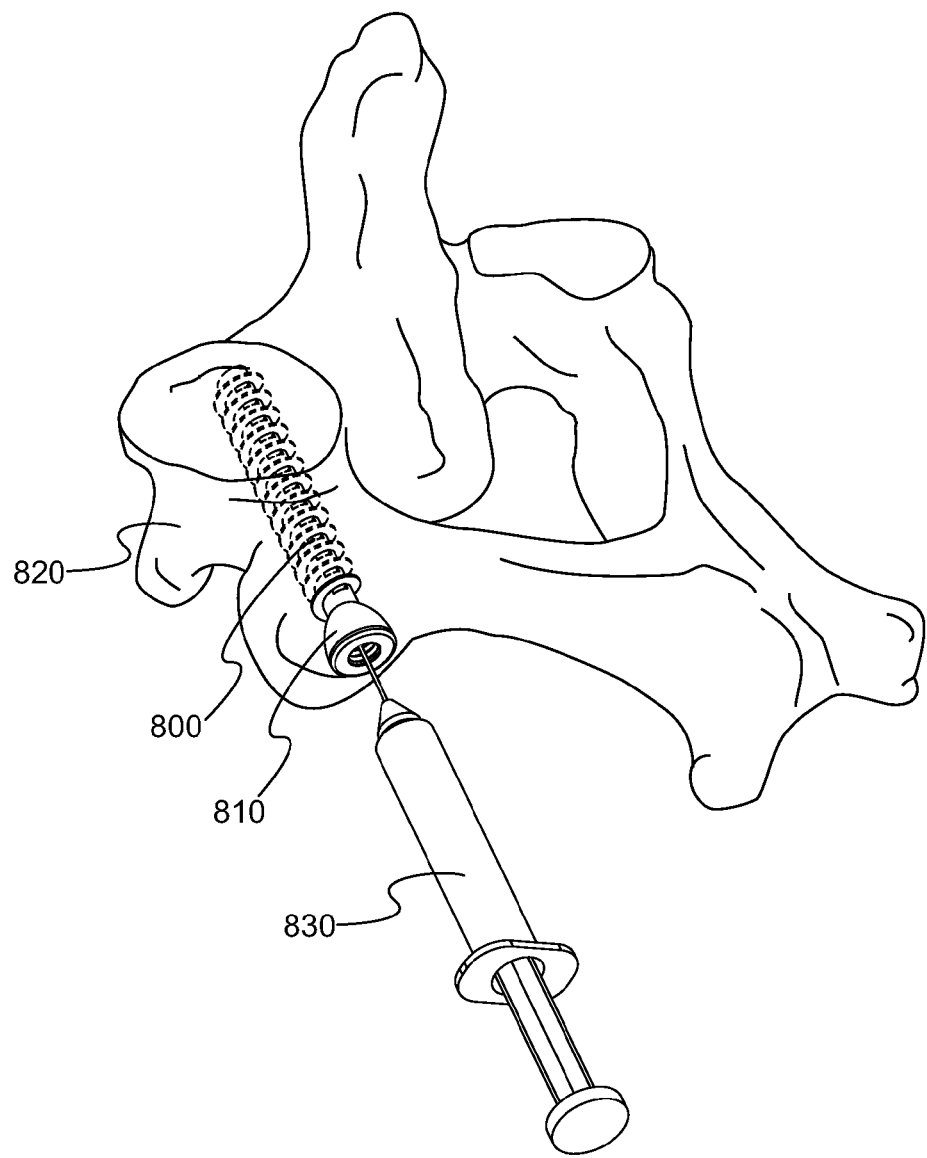
FIG. 8($a$) is a perspective view of a syringe being used to provide a liquid to a bone screw disposed in a hip bone.
Figure 8B:
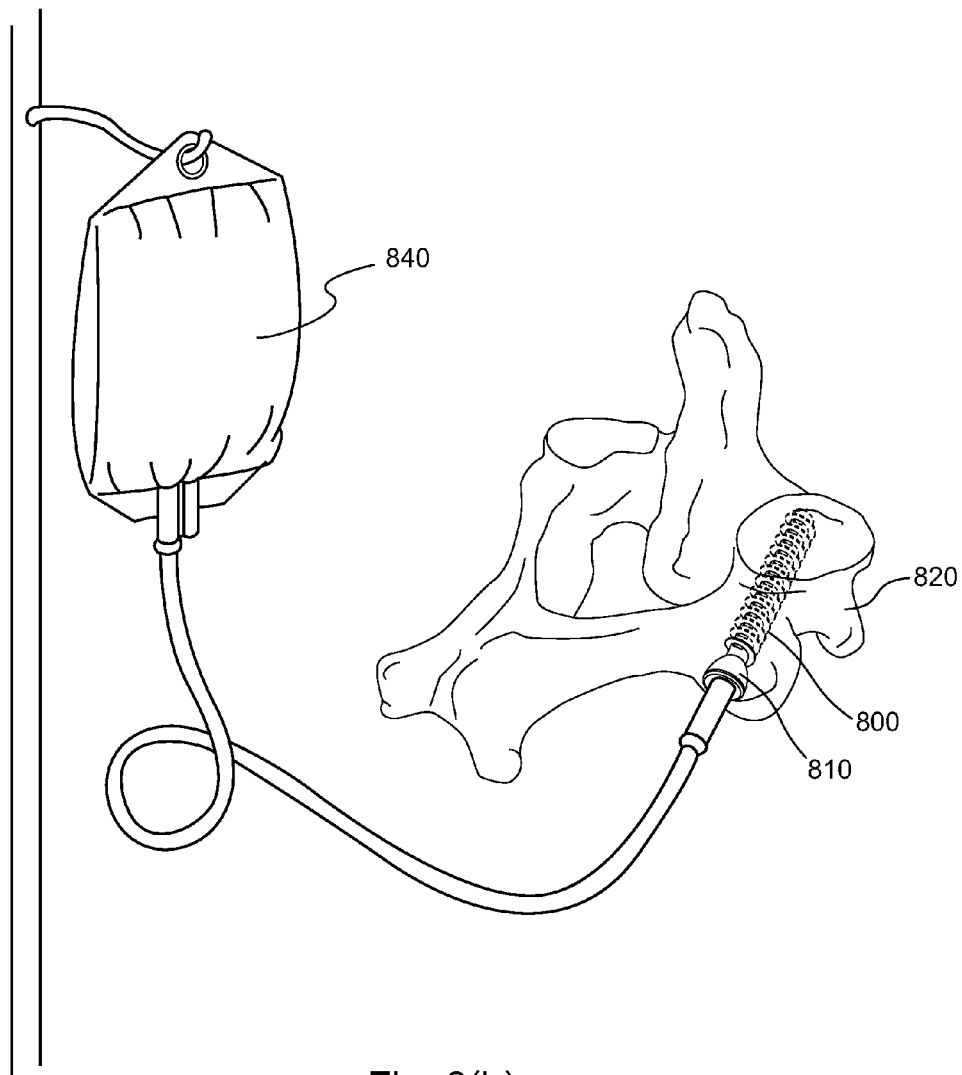

In certain embodiments, it may be desirable that the substance be stored in a reservoir prior to delivery to a bone. For the purposes of this application, the term "reservoir" refers to any source of the one or more substances to be delivered to the vicinity of a bone. For example, the reservoir may be formed from the hollow cavity created by the cannulation of the bone-screw insert and any part of the bone-screw cannulation not occupied by the insert, as depicted in FIG. 7 and described above. In one embodiment, the substance to be delivered may be absorbed into a sponge-like material such as a collagen, for example, which may then be disposed within the cannulated portion of the bone screw or insert, or both. When additional reservoir space is desired, a suitable reservoir may be connected to the cannula opening of either the bone screw or insert. For example, FIG. 8(*a*) shows a bone screw 800 and an insert 810 disposed therein, both of which are disposed within a bone 820. FIG. 8(*a*) further discloses a syringe 830 which acts as a reservoir in accordance with the present invention to provide a substance to the bone 820 via bone screw 800 and insert 810. The bone screw 800 and insert 810 may be configured to allow for re-sealing and multiple time or multiple use access to the cannulated portion of the bone screw 800 or insert 810 through the use of a seal coupled to the outer or proximal end of the insert 810. In one embodiment, the seal may be directly coupled to the inner surface of the insert 810 to seal the outer or proximal end of the insert 810. In other embodiments, the seal may be positioned along the shaft of the insert. In some embodiments, the seal may be removably coupled to the insert 810. In other embodiments, the seal may be coupled to the insert 810 via a non-removable (i.e., permanent) coupling.

Another exemplary embodiment is depicted in FIG. 8(*b*) which discloses an intravenous (IV) bag 840 which serves as a reservoir for delivering a substance to the bone 820 via the bone screw 800 and the insert 810. In yet another embodiment the reservoir may be implanted beneath the patient's skin, i.e., subcutaneously.

Figure 8C:
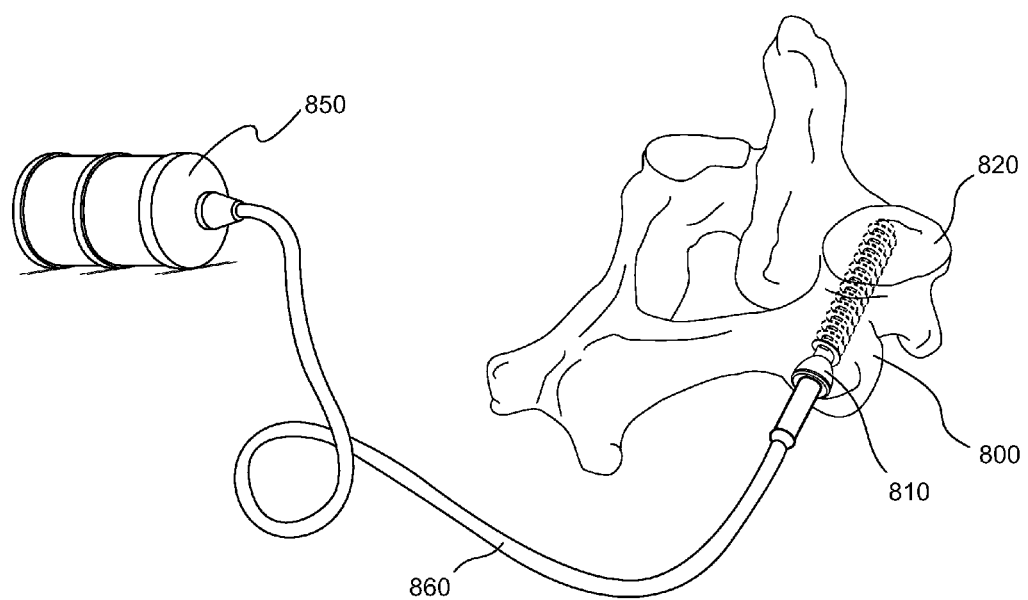

According to another embodiment, the device further includes a pump 850 and tubing 860, as depicted in FIG. 8(*c*), for delivering a substance to the bone 820 via the bone screw 800 and the insert 810. The pump 850 may be utilized to aid in delivery of the substance to the vicinity of the bone 820 by, for example, delivering a continuous, regulated volume to the screw 800. The pump 850 may also be used to increase the fluid pressure within the cannulated portion of the insert 810, thereby aiding fluid flow through the insert fenestrations or insert walls, for example. This embodiment may have the further advantage that the positive pressure created by the pump 850 within the cannulated portion of the insert 810 or bone screw 800 hampers the influx of unwanted materials or compounds into the device. The pump 850 may be connected to the cannulated portion of the bone screw 800 or the insert 810 as depicted in FIG. 8(c). The pump 850 may be implanted subcutaneously if desired to provide long-term care via the delivery of the substance to the bone 820 over an extended period of time. Examples of pumps which may be suitably used in the practice of the current invention are the implantable pumps disclosed in U.S. Pat. No. 4,588,394, for example. Other examples may include external pumps similar to those used with patient controlled anesthesia machines or simple IV pumps.

The fixation of the insert to the bone screw, such as by a threaded connection, a press fit, an external clip, a snap fit, an adhesive, or another suitable fixation means allows for the insert to remain attached to the bone screw to facilitate the continuous, regulated, or long-term delivery of a substance to the bone (e.g., through an insert fenestration and a bone screw fenestration as described above). If left attached to the bone screw for an extended period of time, the insert may be intermittently coated or permeated with antibiotics to reduce the likelihood of infection in the bone. The insert may be further removed and replaced to allow for the treatment or prophylaxis of infection in the bone.

According to various embodiments, a method of delivering a substance to the vicinity of a bone including the steps of attaching a reservoir, a pump, or both, to the bone screws or bone-screw inserts disclosed herein. Such reservoirs and pumps may aid in the continuous, regulated, or long-term delivery of the desired substance to the vicinity of a bone, thereby facilitating the healing process or the overall health of the bone and its surrounding tissues. According to various exemplary embodiments, such a substance may be configured to provide IV fluids, nutrition, antibiotics or chemotherapy to the bone.

Figure 9A:
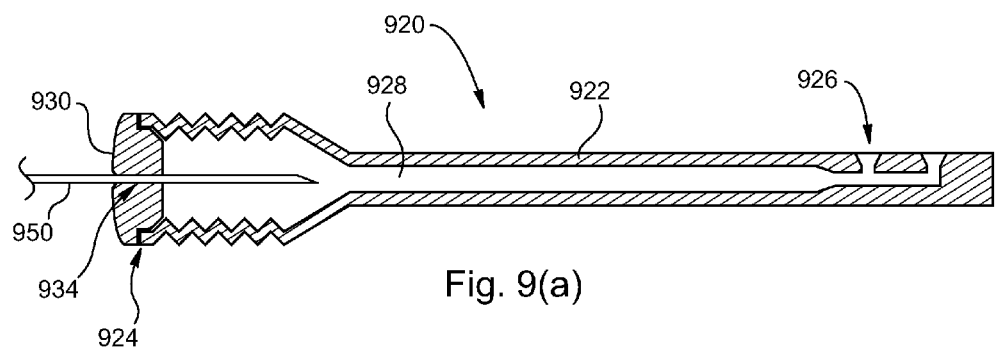
FIG. 9($a$) is a schematic cross-sectional view of a bone-screw insert with a resealing cap, in accordance with the present invention.
Figure 9B:
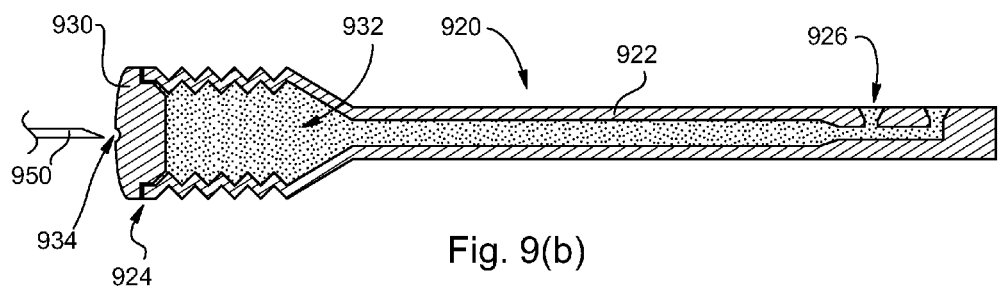

Referring to FIG. 9(a) and FIG. 9(b), a schematic cross-sectional view of an insert 920 is shown according to an exemplary embodiment. The insert 920 includes a shaft 922, an opening 924 located at the proximal end of the insert 920, and at least one insert fenestration 926 located through the shaft 922. The shaft 922 of the insert 920 also includes a cannulation 928 formed along at least a portion of the shaft 922. In the embodiment shown, the opening 924 is located at one end of the cannulation 928. As shown in FIG. 9(a) and FIG. 9(b), the opening 924 of the insert 920 is closed or sealed by a cap 930. The cap 930 is coupled to the outer or proximal end of the insert 920. The cap 930 acts to seal the outer or proximal end of the insert 920. In this arrangement, the cap 930 includes an inner surface facing or in communication with the cannulation 928. The cap 930 may be coupled to or attached to the insert 920 by any suitable means. For example, the cap 930 may be threaded to mate with threads located within the opening 924, and, in other embodiments, the cap 930 may be press fit into the opening 924 or may be attached to the opening 924 with an adhesive. In another embodiment, the opening 924 may be located along the sidewall of the insert, and the cap 930 may seal the opening along the sidewall of the insert. In other embodiments, a seal may be positioned along the shaft of the insert.

As discussed above, a substance may be placed in the cannulated portion of an insert, such as the insert 920, so that the substance may be delivered through the insert fenestrations and through the bone screw fenestrations to the bone. In an exemplary embodiment, the insert cap 930 is able to provide multiple-time or reusable access to the cannulation 928 of the insert following implantation of the bone screw/insert combination into the bone. In the exemplary embodiment of FIG. 9(a) and FIG. 9(b), reusable, post-implantation access to the cannulation 928 of the insert 920 is provided by the self-sealing cap 930. In this embodiment, the cap 930 includes a resilient, self-sealing material. The needle 950 pierces through the cap 930 providing access to the cannulation 928. As shown in FIG. 9(a), the needle 950 creates a perforation 934 that extends through the cap 930. With needle the 950 located within the cannulation 928, a substance 932 may be delivered from the fluid delivery device into the cannulation 928. With the substance 932 within the cannulation 928, the substance 932 may be delivered through the insert fenestrations 926 and through bone screw fenestrations as discussed in the various embodiments above.

As shown in FIG. 9(b), once the substance 932 is delivered to the insert 920, the needle 950 may be removed or withdrawn from the cap 930. Once the needle 950 is withdrawn, the perforation 934 self-seals to prevent the substance 932 from flowing out of the proximal end of the insert 920 through the perforation 934. The process of inserting the needle 950 through the cap 930 may be repeated as necessary to deliver multiple doses of a substance to the insert 920. While the fluid delivery device is shown in FIG. 9 as the syringe 940, in various other embodiments, the needle 950 may be connected to a variety of fluid delivery devices. For example, the fluid delivery device may be a pump (e.g., an infusion pump) or a bag or reservoir or fluid bag (similar to an IV bag) coupled to the needle 950 via tubing. In one embodiment, the fluid delivery device may be a micro-infusion device in fluid communication with the cannulated portion of the insert and/or bone screw. In this embodiment, the micro-infusion pump may be worn by a user, and a substance may be continuously delivered through the bone screw and/or insert to promote bone growth.

In various embodiments, the cap 930 may be made from any material or combination of materials that provide for resealing or self-sealing. In various embodiments, the cap 930 may be made from a compliant, non-rigid or resilient material that resiliently expands following withdrawal of the needle 950 to the seal perforation 934 caused by the needle 950. In one embodiment, the cap 930 may be made from a surgical, self-sealing rubber or polymer, such as surgical silicone rubber.

The post-implantation access to the cannulation 928 of the insert 920 provided by the cap 930 may allow the user to deliver a new or second substance or additional doses of a same substance to the bone as needed to treat a particular patient. For example, following implantation of the bone screw/insert combination, separate doses of antibiotics may be delivered to a fracture site via the insert 920. In another embodiment, the insert 920 may be used for repeated delivery of cancer treating drugs to the bone in which the bone screw is implanted. In another embodiment, bone morphogenic proteins may be delivered in separate doses to the bone via the insert 920. In other embodiments, any other substance that may be intermittently delivered to a patient may be delivered using the insert 920. Further, in contrast to single-use delivery devices, repeatable access and multiple time delivery via the insert 920 may be useful in adjusting or changing the substances delivered via the insert 920. For example, the insert 920 and the resealing cap 930 allow the user to change either the dose or the type of substance delivered to a patient each time the needle 950 is inserted through the cap 930. In addition, post-implantation access to the cannulation 928 of the insert 920 by the needle 950 may allow for the post-implantation connection of any desired fluid delivery device (e.g., an IV or infusion pump) to the insert by connecting the fluid delivery device to the needle 950. This may allow the user to switch or change the type of fluid delivery device used to deliver fluid to the bone via the bone screw/insert combination. In other embodiments, the needle 950 may also be connected to a material removal device allowing for repeat and resealing access through the cap 930 for removal of material from the cannulation 928 of the insert 920.

To deliver a dose of a substance to a patient by piercing the cap 930 with the needle 950, the needle 950 is aligned with the cap 930 following implantation of the implanted bone screw/insert combination. In some embodiments, the bone screw/insert combination may be located a small distance below the skin such that the cap 930 may be palpated through the skin allowing a user to align the needle with the cap 930 by touch. In other embodiments, the bone screw/insert combination may be located in a bone deeper below the skin such that alignment via palpation may be difficult or impossible. In such an embodiment, the needle 950 may be aligned with the cap 930 by imaging the location of the cap 930 via a suitable imaging device (e.g., via X-ray, CT, etc.).

Figure 10:
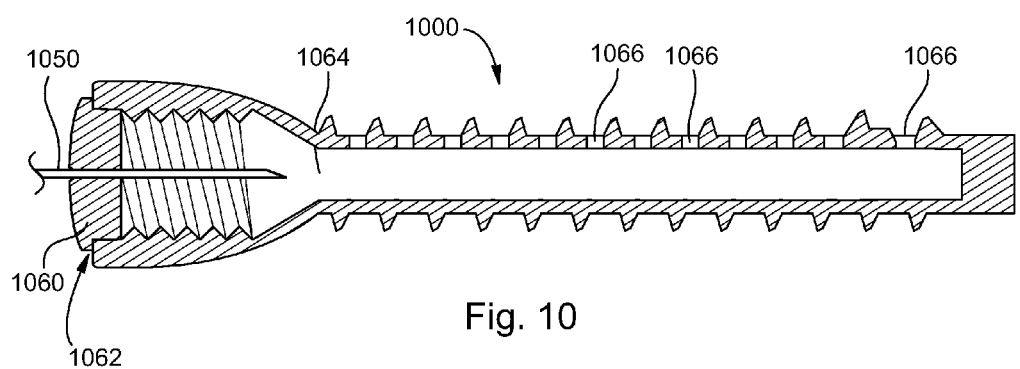
FIG. 10 is a schematic cross-sectional view of a bone screw with a resealing cap, according to an exemplary embodiment.

While the embodiment shown in FIGS. 9(*a*) and 9(*b*) shows the resealing cap coupled to an insert, it should be understood that in other embodiments the cap may be coupled directly to a cannulated bone-screw to seal the proximal opening of a bone-screw. For example, as shown in FIG. 10, a bone screw 1000 may include a resealing cap, shown as a bone screw cap 1060 (similar to the cap 930), that is coupled to or attached to the bone screw 1000 such that the bone screw cap 1060 seals the proximal opening 1062 of the bone screw 1000. Similar to the other bone screw embodiments discussed herein, the bone screw 1000 includes a bone screw cannulation 1064 and bone screw fenestrations 1066. With the needle 1050 extending through the cap 1060, material may be delivered to a bone through the bone screw fenestrations 1066, and, as discussed below, material may be removed from the bone through the bone screw fenestrations 1066. As shown in FIG. 10, the bone screw cap 1060 may seal the bone screw 1000 without an insert disposed within a bone screw cannulation 1064. In another embodiment, the bone screw cap 1060 may seal the proximal opening 1062 of the bone screw 1000 with an insert disposed within the bone screw cannulation 1064. Further, it should be understood that various embodiments of the resealing caps 930, 1060 may be used with any of the bone screw and insert embodiments discussed herein.

Figure 11:
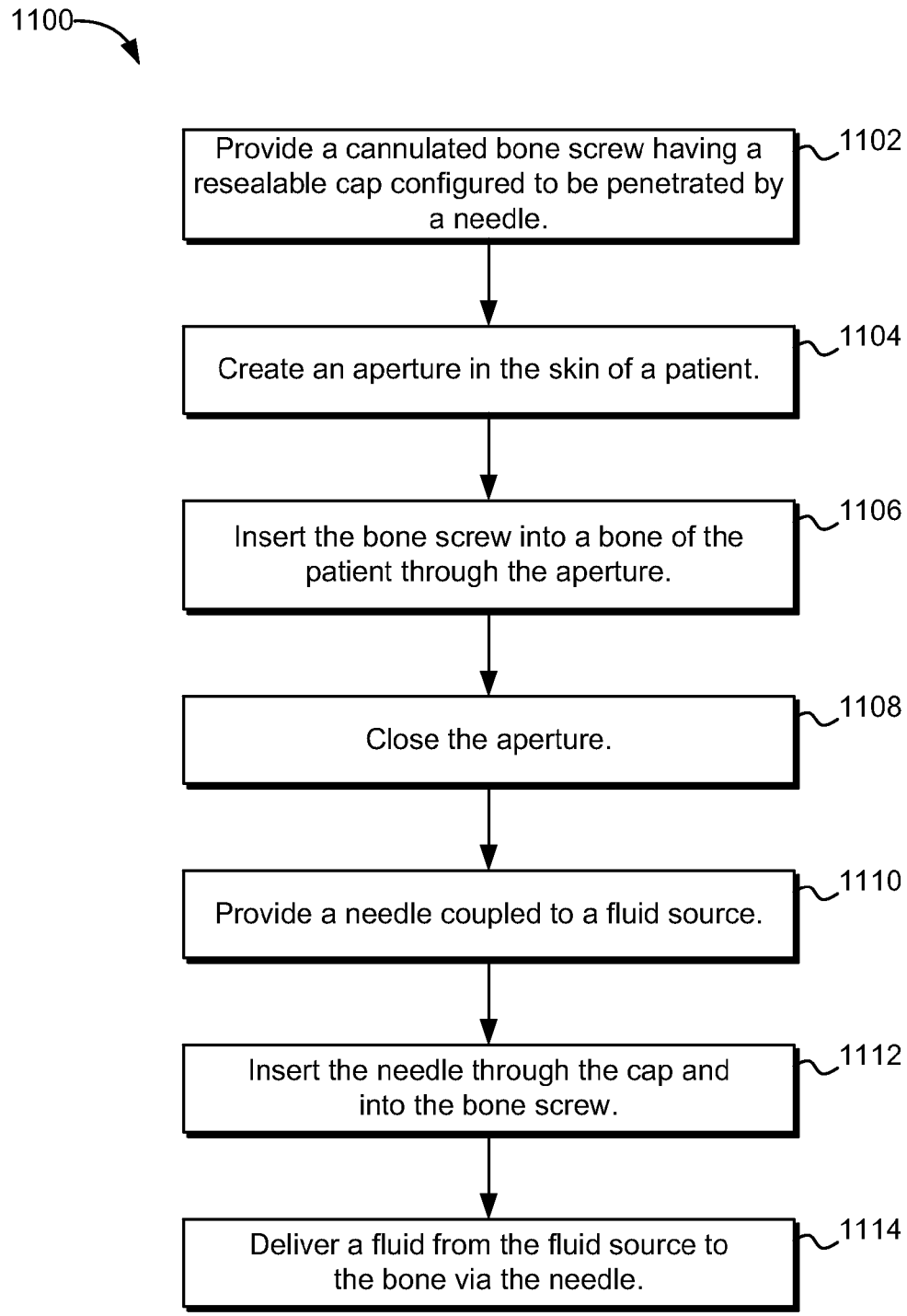
FIG. 11 is a flow chart of a method for the long-term delivery of fluids to a bone of a patient, according to an exemplary embodiment.

Referring now to FIG. 11, a method 1100 for the long-term delivery of a substance to a bone of a patient is shown according to an exemplary embodiment. A cannulated bone screw is provided, with the bone screw having a resealable cap coupled to one end (step 1102). The bone screw may include various fenestrations to allow for a substance to be delivered from the cannulated portion of the bone screw to the bone. The cap is configured to be penetrated by a needle and may be made from a compliant, non-rigid or resilient material that can seal a perforation caused by the needle. An aperture is created in the skin (e.g., an incision through the skin and other tissue layers) of the patient to provide access to the bone (step 1104). The bone screw is inserted into the bone of the patient through the aperture (step 1106). In certain situations, it may be advantageous to drill a pilot hole in the one or more bones or bone pieces in order to facilitate introduction of the bone screw. In this regard it may be found advantageous to use bone screws with self-tapping threads, or to pre-cut the threads in the bone prior to bone screw insertion. The aperture is then closed (step 1108). In one exemplary embodiment, the aperture may be closed over the top of the bone screw such that the bone screw remains implanted subcutaneously. In another exemplary embodiment, the aperture may be closed with the proximal end of the bone screw protruding through the skin. A fluid source containing a fluid to be provided to the bone is provided with the fluid source coupled to a needle capable of penetrating the cap coupled to the bone screw (step 1110). The fluid source may be, for example, a reservoir in the form of a syringe, an IV bag, or a pump. The needle is inserted through the cap and into the cannulated bone screw (step 1112). The fluid is then delivered from the fluid source through the needle and into the bone screw (step 1114).

The method may further include coupling an insert to the bone screw prior to closing the aperture. The insert may be a cannulated, fenestrated insert as described in several exemplary embodiments above. The insert is positioned to deliver a fluid to the bone screw. Under some circumstances, it may be advantageous to introduce the insert into or along the bone screw, in its entirety or only partially, prior to introducing the bone screw into the bone. This sequence might be preferred in order to shorten the overall surgery time, or to reduce the amount of material that enters the bone-screw fenestrations from outside the screw during screw insertion, for example. Alternately, other circumstances may make it more advantageous to introduce the insert into the bone screw, in its entirety or only partially, after the bone screw is introduced into the bone. This latter sequence might be preferred in order to be able to determine which screw fenestrations or exterior insert attachment mechanisms (e.g. grooves) are located at the optimum location for delivery of the desired substance (e.g., the fluid provided from the fluid source), and thus what insert configuration or length should be used to facilitate substance delivery to desired locations in or near a bone. Other methods may include partially introducing the bone screw into a bone, partially or completely inserting the insert into or along the bone screw, and then completing the insertion of the bone screw into the bone. All such sequence variations are to be included within the scope of this disclosure.

The method may further include removing the insert without removing the bone screw, heating the insert, and reinserting the insert into the bone screw cannulation to heat the bone screw and the area proximate the bone screw. Heat may be applied to the portion of the bone surrounding the bone screw, for example, to facilitate the curing of bone cement deposited in the bone.

Figure 12:
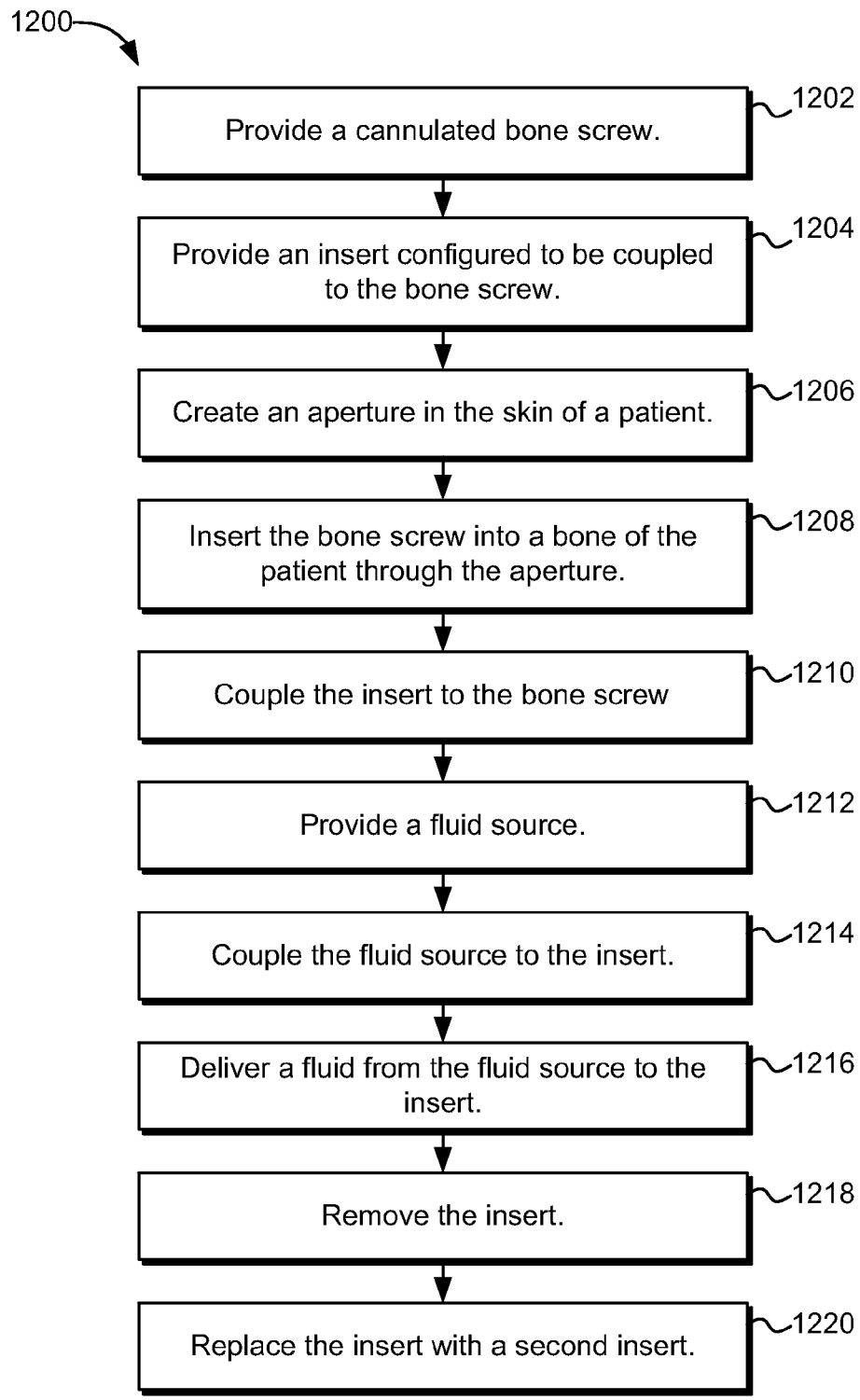
FIG. 12 is a flow chart of a method for the long-term delivery of fluids to a bone of a patient, according to an exemplary embodiment.

Referring now to FIG. 12, a method 1200 for the long-term delivery of a substance to a bone of a patient is shown according to another exemplary embodiment. A cannulated bone screw (step 1202) and an insert configured to be coupled to the bone screw are provided (step 1204). The bone screw and the insert may include various fenestrations to allow for a substance to be delivered from the cannulated portion of the bone screw and the insert to the bone. An aperture is created in the skin (e.g., an incision through the skin and other tissue layers) of the patient to provide access to the bone (step 1206). The bone screw is inserted into the bone of the patient through the aperture (step 1208). In certain situations, it may be advantageous to drill a pilot hole in the one or more bones or bone pieces in order to facilitate introduction of the bone screw. In this regard it may be found advantageous to use bone screws with self-tapping threads, or to pre-cut the threads in the bone prior to bone screw insertion. The insert is coupled to the bone screw (step 1210). The insert is positioned to deliver a fluid to the bone screw. Under some circumstances, it may be advantageous to introduce the insert into or along the bone screw, in its entirety or only partially, prior to introducing the bone screw into the bone. The insert may be treated with an antibiotic treatment prior to coupling the insert to the bone screw to inhibit the growth of bacteria and reduce the likelihood of infection in the bone.

A fluid source is provided containing a fluid to be provided to the bone (step 1212). The fluid source may be, for example, a reservoir in the form of a syringe, an IV bag, or a pump. The fluid source is then coupled to the insert (step 1214), such as by a tube in fluid communication with the fluid source and the insert. The fluid is then delivered from the fluid source to the insert (step 1216).

According to an exemplary embodiment, the bone screw is configured to be inserted into a bone for an extended period to provide long-term therapy to the bone. By providing a coupling mechanism such as threads 340 to fix the insert to the bone screw, the insert is stabilized to facilitate the long term delivery of fluid or another substance to the bone. The fluid may be delivered at a constant rate (e.g., through a porous wall in the insert or bone screw or through constant saturation) or may be delivered intermittently in discreet doses (e.g., every four hours) as long as the insert is coupled to the bone screw. The method further includes removing the insert from the bone screw (step 1218). According to an exemplary embodiment, the insert is removed from the bone screw at least one week after commencement of delivery of the fluid from the fluid source. According to a preferred embodiment, the insert is removed from the bone screw at least one month after commencement of delivery of the fluid from the fluid source. According to a particularly preferred embodiment, the insert is removed from the bone screw after commencement of delivery of the fluid from the fluid source. The insert is then replaced with a second insert coupled in the bone screw (step 1220). The second insert may be treated with an antibiotic treatment prior to coupling the insert to the bone screw to inhibit the growth of bacteria and reduce the likelihood of infection in the bone. The inserts may continue to be replaced periodically to continue the long-term therapy of the bone.

The method may further include closing the aperture in the skin of the patient. In one exemplary embodiment, the aperture may be closed over the top of the bone screw such that the bone screw is disposed beneath the skin and remains implanted subcutaneously. In another exemplary embodiment, the aperture may be closed with the proximal end of the bone screw or insert protruding through the skin.

In an exemplary embodiment, a method of administering a substance to a bone includes introducing a cannulated, fenestrated bone screw into a bone, introducing a cannulated insert into the bone screw, and introducing a substance to be delivered into the cannulated portion of the insert. In another embodiment, the method includes attaching a cannulated insert along at least a portion of an exterior surface of a bone screw, introducing the bone screw into a bone, and introducing a substance to be delivered into the cannulated portion of the insert.

In an exemplary embodiment, a method for delivering heat to an area surrounding a bone screw includes inserting an insert into the bone screw cannulation, removing the insert without removing the bone screw from the bone, heating the insert, and reinserting the insert into the bone screw cannulation to heat the bone screw and area of the bone proximate the bone screw. According to an exemplary embodiment, the insert may protrude through a fenestration in a distal end of the bone screw to extend into an area of the bone beyond a distal end of the bone screw.

When the bone screw is a fixation screw, a method of holding or fixing two or more bones or bone pieces in a fixed spatial relationship with respect to each other may be used. Such a method may be desirable when it is desired to deliver a substance such as a medicant or therapeutic to the vicinity of a site where a peripheral skeletal fracture or an osteotomy is mended, a spondyloysis or an odontoid fracture repaired, or lumbar facet joints are fused.

In one embodiment, the bone screw may be a fixation nail that holds two or more bones or bone parts in a fixed spatial relationship. In this embodiment the exterior of the bone screw shaft is unthreaded. The fixation nail may be adapted for use in the fixation of a variety of bones, including, but not limited to, femur fixations, humerus fixations and tibia fixations.

The inserts and methods of use thereof may be used with a wide variety of cannulated bone screws, fixation nails, and the like. Various exemplary bone screws and fixation nails are disclosed in U.S. Published Application No. 2012/0041395, which is incorporated by reference herein.

In alternative exemplary embodiments, inserts as disclosed herein may be used without a bone screw, to be directly inserted into a bone such as for purposes of irrigating the bone with antibiotics, saline, other medicines, or other fluids prior to screw placement. In some embodiments, the insert may be placed directly into a bone via guide wire placement or reaming, without a bone screw or other intermediate device between the insert and bone. The insert may include expandable portions to control the flow of fluids directly between the bone and insert. The expandable portions of such inserts may be mechanically expanded, inflated, or predisposed to expand and released in a controlled manner.

While in some embodiments disclosed herein the insert is cannulated and has a single passage for communication of fluids, in other embodiments the insert may include a second conduit for suction of fluids after irrigation. As such, one passage may provide fluid while the other passage concurrently removes fluid. Following irrigation, the insert may be removed and a bone screw may then be inserted into the irrigated opening in the bone. The same insert or another insert, may then be inserted into bone screw to deliver medications or other fluids. Such a process may be particularly beneficial for treating open long-bone fractures.

In some embodiments, inserts disclosed herein may be used with devices other than bone screws. In some such embodiments, inserts are positioned in nails or other fastening devices. Furthermore, various fluids may be used with the inserts and bone screws disclosed herein, including saline, antibiotics, glue, and other fluids.

Further modifications and alternative embodiments of various aspects of the invention will be apparent to those skilled in the art in view of this description. Accordingly, this description is to be construed as illustrative only. The construction and arrangements of the bone screws and inserts, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A method for long-term delivery of fluids to a bone of a patient, comprising:
    providing a bone screw having a cannulation, and having one or more threads disposed on a proximal end of the bone screw;
    providing an insert having one or more threads disposed on a proximal end of the insert configured to be coupled to the bone screw, wherein the one or more threads on the insert are configured to engage with the one or more threads on the bone screw;
    creating an aperture in skin of the patient;
    inserting the bone screw into the bone of the patient through the aperture;
    inserting a distal end of the insert through the cannulation in the bone screw and coupling the one or more threads on the proximal end of the insert to the one or more threads on the proximal end of the bone screw;
    providing a fluid source;
    coupling the fluid source to the insert;
    delivering a fluid from the fluid source to the insert;
    removing the insert without removing the bone screw;
    treating the insert with a treatment intended to reduce infection in the bone; and
    recoupling the treated insert to the bone screw.

2. The method of claim 1, wherein the insert is received within the bone screw cannulation, and further comprising:
    heating the insert;
    reinserting the insert into the bone screw cannulation to heat an area proximate the insert.

3. The method of claim 1, further comprising treating the insert with an antibiotic treatment prior to coupling the insert to the bone screw.

4. The method of claim 1, wherein the insert at least partially protrudes through the skin when coupled to the bone screw.

5. The method of claim 1, further comprising closing the aperture over the insert wherein the insert remains disposed beneath the skin.

6. The method of claim 1, further comprising removing the insert from the bone screw.

7. The method of claim 6, wherein the removing step is performed more than one week after commencing the delivering step.

8. The method of claim 6, wherein the removing step is performed more than one month after commencing the delivering step.

9. The method of claim 6, further comprising providing a second insert and coupling the second insert to the bone screw.

10. The method of claim 1, wherein the fluid comprises one or more of an IV fluid, an antibiotic fluid, a parenteral nutrition fluid, a chemotherapy agent, or a bone cement.

11. A method for long-term delivery of fluids to a bone of a patient, comprising:
    providing a bone screw having a cannulation, and having one or more threads disposed on a proximal end of the bone screw;
    providing an insert having one or more threads disposed on a proximal end of the insert configured to be coupled to the bone screw, wherein the one or more threads on the insert are configured to engage with the one or more threads on the bone screw;
    creating an aperture in skin of the patient;
    inserting the bone screw into the bone of the patient through the aperture;
    inserting a distal end of the insert through the cannulation in the bone screw and coupling the one or more threads on the proximal end of the insert to the one or more threads on the proximal end of the bone screw;
    providing a fluid source;
    coupling the fluid source to the insert; and
    delivering a fluid from the fluid source to the insert;
    wherein the insert at least partially protrudes through the skin when coupled to the bone screw.

* * * * *